(12) United States Patent
Steiner et al.

(10) Patent No.: US 7,935,152 B2
(45) Date of Patent: May 3, 2011

(54) HINGED CONNECTING APPARATUS FOR A LOWER LIMB PROSTHESIS

(75) Inventors: Jean-Louis Steiner, Moutier (CH); Clement Schneider, Le Landeron (CH)

(73) Assignee: S & S Sarl, Moutier (CH)

( * ) Notice: Subject to any disclaimer, the term of this patent is extended or adjusted under 35 U.S.C. 154(b) by 0 days.

(21) Appl. No.: 12/300,022

(22) PCT Filed: May 10, 2006

(86) PCT No.: PCT/EP2006/062217
§ 371 (c)(1),
(2), (4) Date: Nov. 7, 2008

(87) PCT Pub. No.: WO2007/128351
PCT Pub. Date: Nov. 15, 2007

(65) Prior Publication Data
US 2009/0187260 A1  Jul. 23, 2009

(51) Int. Cl.
*A61F 2/64* (2006.01)
(52) U.S. Cl. .................. 623/40; 623/43; 623/44; 623/45
(58) Field of Classification Search ............... 623/39–46
See application file for complete search history.

(56) References Cited

U.S. PATENT DOCUMENTS

| | | | |
|---|---|---|---|
| 2,170,580 A | 2/1937 | Steele et al. | |
| 4,179,759 A | 12/1979 | Smith | |
| 6,613,097 B1 * | 9/2003 | Cooper | ........................... 623/44 |
| 6,755,870 B1 * | 6/2004 | Biedermann et al. | ........... 623/24 |
| 2007/0027555 A1 * | 2/2007 | Palmer et al. | .................... 623/24 |

FOREIGN PATENT DOCUMENTS

| | | |
|---|---|---|
| DE | 325579 | 9/1920 |
| DE | 880191 C | 6/1953 |
| DE | 3028608 A1 | 2/1982 |
| EP | 0549855 A2 | 7/1993 |
| FR | 2741526 A1 | 5/1997 |
| GB | 1007431 A | 10/1965 |
| WO | 01/37763 A1 | 5/2001 |

OTHER PUBLICATIONS

International Search Report, May 24, 2007.

* cited by examiner

*Primary Examiner* — Bruce E Snow
(74) *Attorney, Agent, or Firm* — Pearne & Gordon LLP

(57) ABSTRACT

Hinged connecting apparatus (1) for a lower limb prosthesis (2), the hinged connecting apparatus (1) comprising a first device (1000) intended to oppose a predetermined resistance during flexion of the prosthesis (2), this resistance being switched by said first device (1000) between two values which are a predetermined minimal value and a predetermined maximal value.

11 Claims, 4 Drawing Sheets

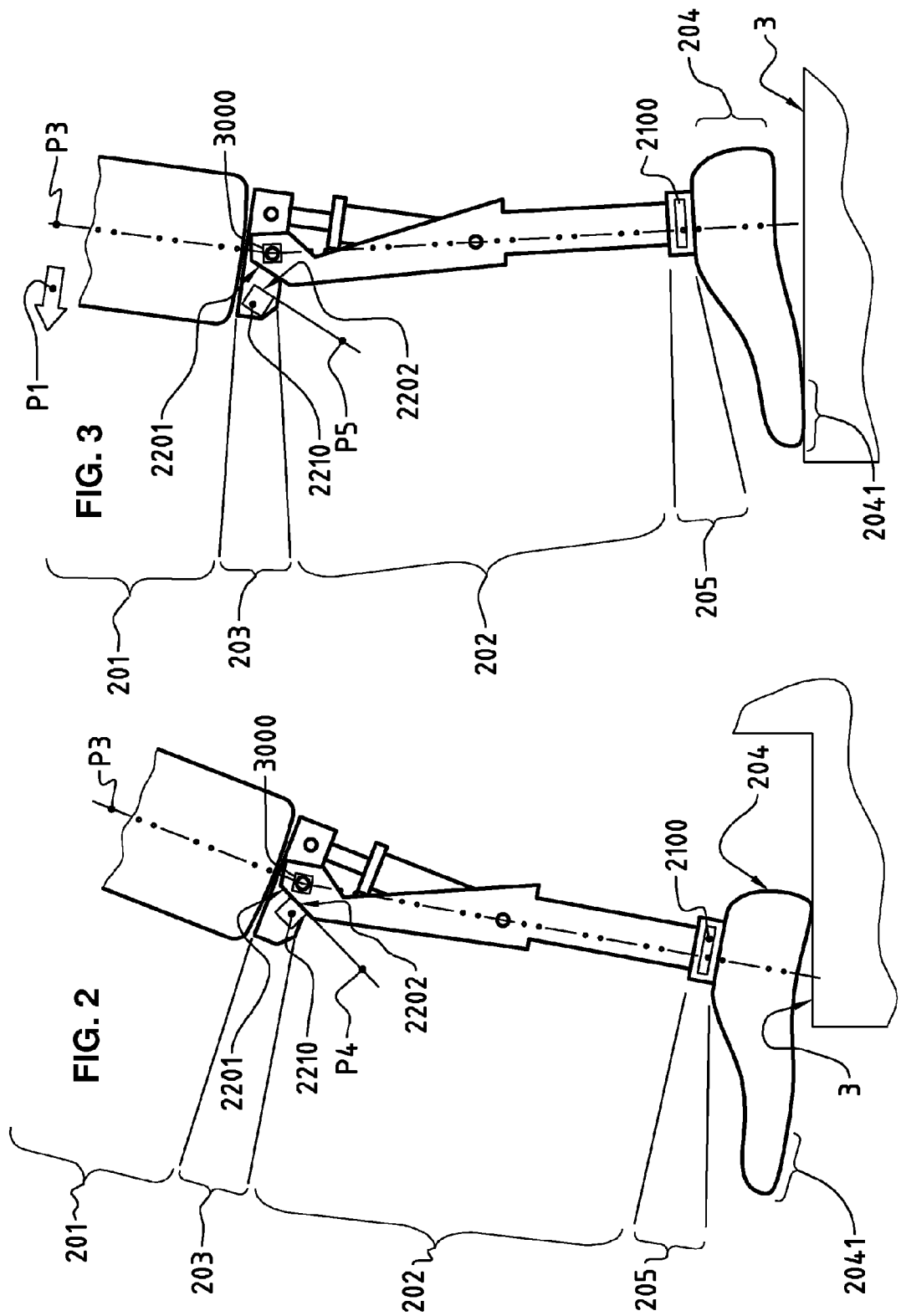

HINGED CONNECTING APPARATUS FOR A LOWER LIMB PROSTHESIS

The invention relates to a hinged connecting apparatus for a lower limb prosthesis.

The invention likewise relates to a prosthesis provided with the aforementioned connecting apparatus.

A prosthesis for a lower limb with hinged connection generally comprises:
- a first part capable of ensuring a thigh function,
- a second part capable of ensuring a leg function,
- a third part capable of ensuring a knee function,
- a fourth part capable of ensuring a foot function with a view to supporting it on a support.

The invention can be used such that the knee is of monocentric type, i.e. with a single axis of articulation, or of polycentric type, i.e. with a plurality of axes of articulation.

The hinged connecting apparatus is incorporated in the third part in such a way as to ensure the articulated connection between the first part and the second part, and this between two relative positions which are:
- a first position in which the first part and the second part extend substantially in the prolongation one of the other, forming a first angle, and
- a second position in which the first part and the second part form a second predetermined angle corresponding to the maximal flexion permitted by the prosthesis.

The hinged connecting apparatus comprises a first device intended to oppose a predetermined resistance at least during the flexion of the prosthesis, this resistance being switched by said first device between two values which are:
- a predetermined maximal value selected by default, and
- a predetermined minimal value selected when the first part and the second part, having been situated in a third position adjacent to the first position, are pulled towards the first position and are moved into this first position.

When the prosthesis is worn by a person, i.e. the first part is connected to an existing part of thigh, the person must be able to change the configuration of the prosthesis and in particular:
- to raise the first part to force the prosthesis to bend and stretch to place said first part and the second part in the second position,
- to press on the first part while the fourth part is in contact with a support and to stretch to place said first part and the second part in the first position.

The known hinged connecting apparatuses have their advantages, but one faults them for not ensuring the complete safety of the person who wears them, in particular when this person must descend an inclined surface, a step or stairway.

One result which the invention aims to obtain is precisely an apparatus that makes it possible to overcome this drawback.

The invention likewise has as subject matter a prosthesis for a lower limb provided with the aforementioned connecting apparatus.

Figure 1:
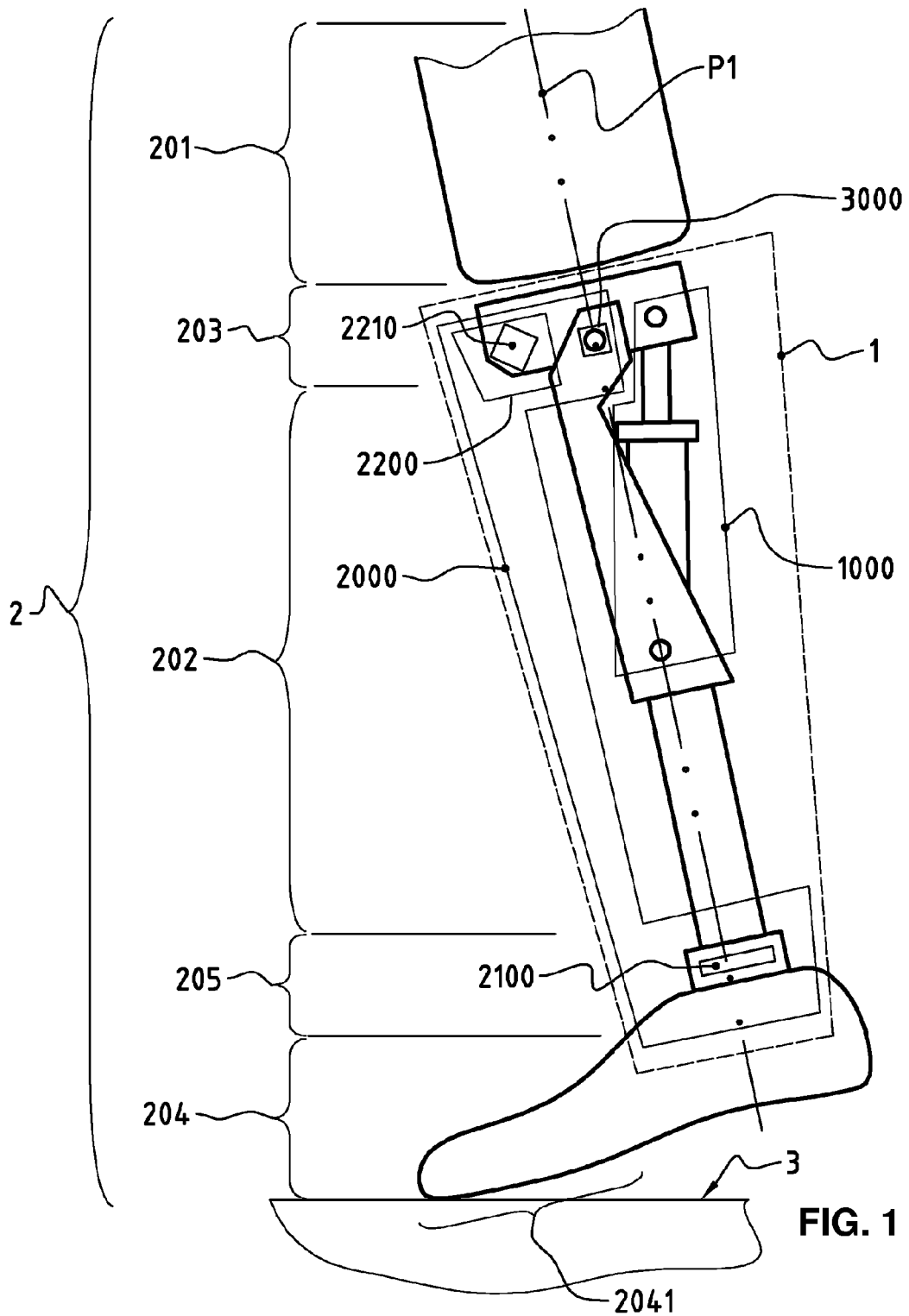
Figure 4:
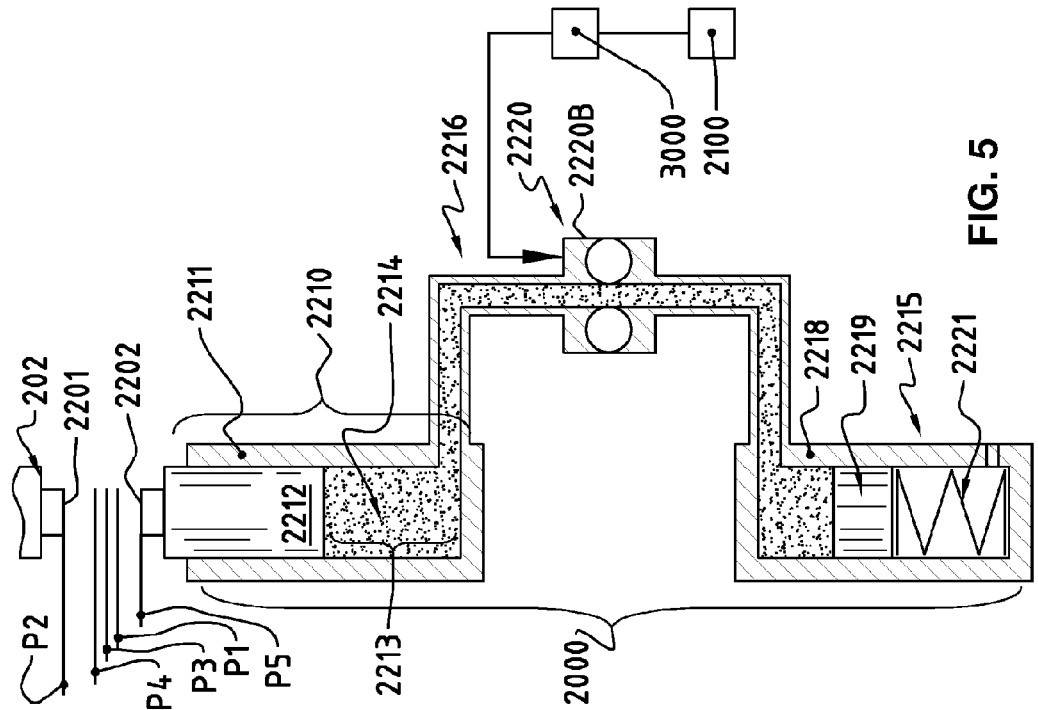
Figure 5:
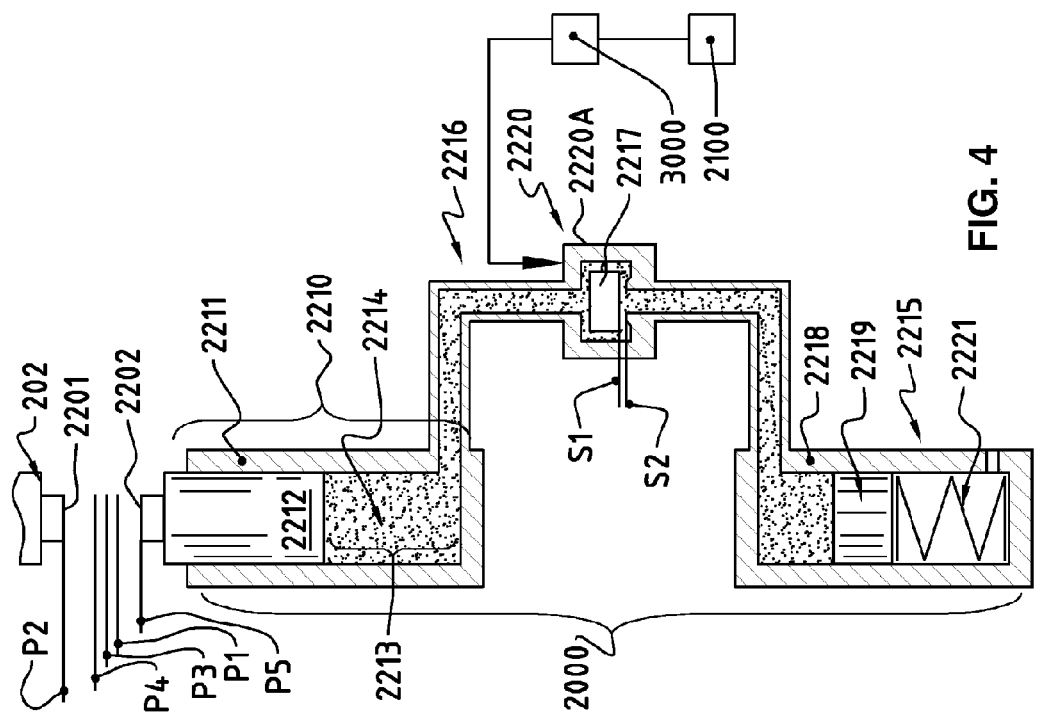
Figure 6:
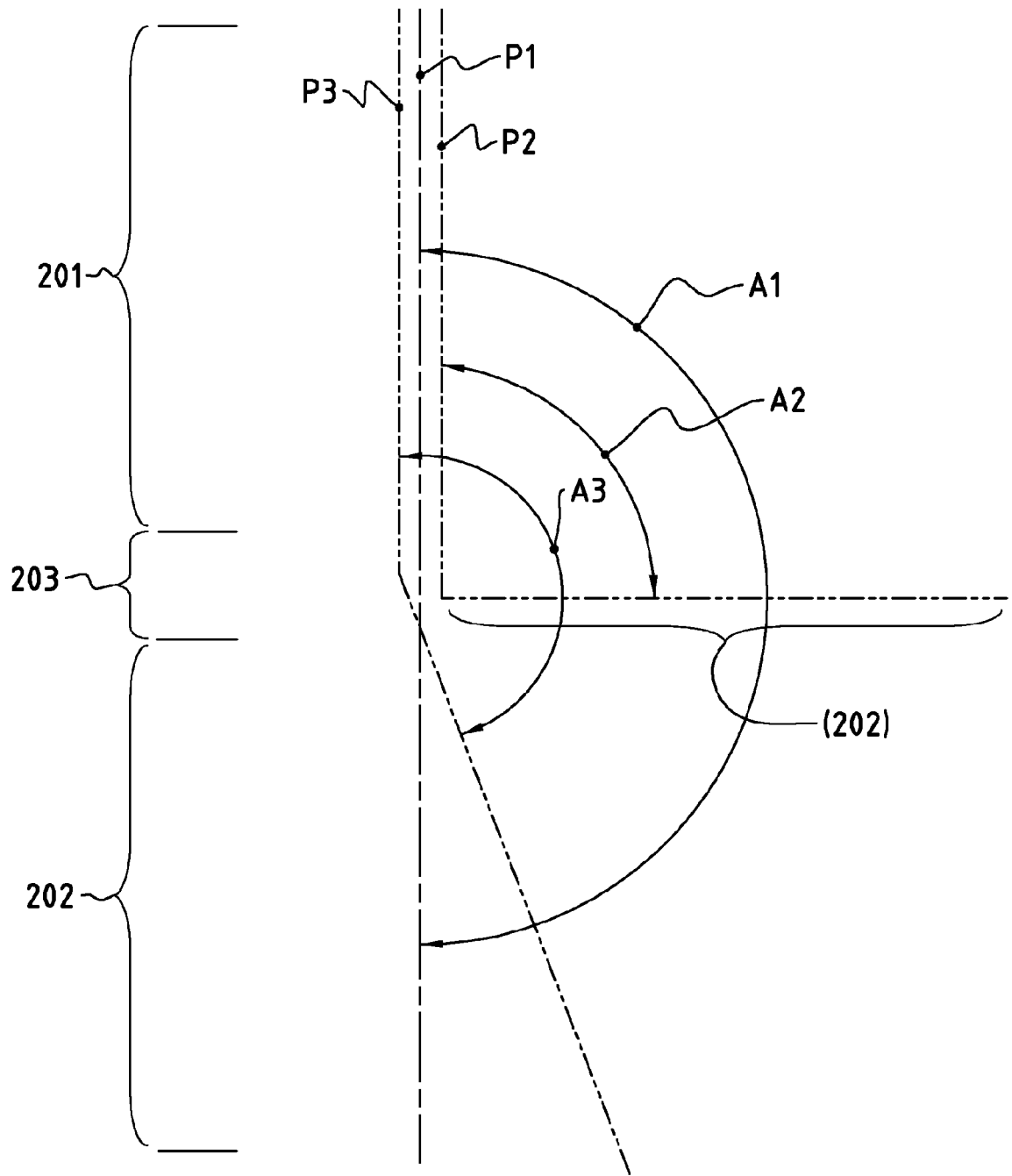

The invention will be well understood from reading the following description, given by way of non-limiting example, with reference to the attached drawing representing schematically:

FIGS. 1 to 3: side views of a prosthesis for a lower limb in different configurations of functioning, FIGS. 4 and 5: seen in section, a device used in the apparatus according to the invention, according to two embodiments, FIG. 6: a simplified view showing the different relative positions of parts of the prosthesis.

Referring to the drawing, one sees a hinged connecting apparatus 1 for a prosthesis 2 for a lower limb.

Conventionally, the prosthesis 2 comprises:
- a first part 201 capable of ensuring a thigh function,
- a second part 202 capable of ensuring a leg function,
- a third part 203 capable of ensuring a knee function,
- a fourth part 204 capable of ensuring a foot function with a view to supporting it on a support 3.

The hinged connecting apparatus 1 is incorporated in the third part 203 in such a way as to ensure the hinged connection between the first part 201 and the second part 202, and this between at least two relative positions which are:
- a first position P1 in which the first part 201 and the second part 202 extend substantially in the prolongation one of the other, forming a first angle A1, and
- a second position P2 in which the first part 201 and the second part 202 form a second predetermined angle A2 corresponding to the maximal flexion permitted by the prosthesis 2.

Said differently, the first position P1 is the configuration for extension of the prosthesis 2, i.e. the configuration in which the first part 201 and the second part 202 form a first angle A1 which is the widest angle that they can adopt.

In this first angle A1, the prosthesis 2 permits a person (not represented) to hold himself in standing position.

Likewise, the second position P2 is the configuration for flexion of the prosthesis 2, i.e. the configuration in which the first part 201 and the second part 202 form a second angle A2, which is the narrowest angle that they can adopt.

In this second angle A2, the prosthesis 2 permits a person (not represented) to hold himself at least in sitting position, or in substantially squatting position.

The hinged connecting apparatus 1 comprises a first device 1000 intended to oppose a predetermined resistance at least during the flexion of the prosthesis 2, this resistance being switched by said first device (1000) between two values which are:
- a predetermined maximal value selected by default, and
- a predetermined minimal value selected when the first part 201 and the second part 202, being situated in a third position P3 adjacent to the first position P1, are pulled towards the first position P1 and are moved into this first position P1.

When the prosthesis is worn by a person (not represented), i.e. the first part 201 is connected to a remaining part of thigh, the person must be able to change the configuration of the prosthesis 2 and in particular:
- to raise the first part 201 to force the prosthesis 2 to bend and stretch to place said first part 201 and the second part 202 in the second position P2,
- to press on the first part 201 while the fourth part 204 is in contact with a support 3 and to stretch to place said first part 201 and the second part 202 in the first position P1.

The third position P3 is a position of the prosthesis 2 which is adjacent to the extension configuration.

In the third position, the first part 201 and the second part 202 form a third angle A3 which is less than the first angle A1 by some degrees, for example by one point five degrees.

The apparatus 1 according to the invention comprises a second device 2000 including at least:
- a first functional means 2100 capable of detecting the bearing of the fourth part 204 on a support 3, at least by a first zone 2041 of this fourth part 204 which corresponds to the front of a foot, and
- a second functional means 2200 capable
  - of impeding the movement of the first part 201 and the second part 202 towards the first position P1 when, on the one hand, they are situated in a third position P3 adjacent to the first position P1 and they are pulled towards said first position P1 and on the other hand, the first functional means 2100 does not detect the bearing of the fourth part 204 on a support 3 by said first zone 2041, of allowing the movement of the first part 201 and the second part 202 towards the first position P1 when, on the one hand, they are situated in a third position P3 adjacent to the first position P1 and they are pulled toward the first position P1 and, on the other hand, the first functional means 2100 detects the bearing of the fourth part 204 on a support 3 by said first zone 2041 of the fourth part 204 (This latter situation is illustrated in FIG. 3, and the possibility of passage from the third position P3 to the first position P1 is symbolized by an arrow mark P1).

This way the prosthesis 2 cannot bend freely and in a way detrimental to the person wearing it, particularly when this person must descend one or more steps by leaning alternately on the prosthesis 2.

In fact, the second means 2200 prevents the prosthesis 2 from being able to bend freely when it is pulled towards the extension configuration, but when no support has been detected at the level of the first zone 2041 corresponding to the front of a foot.

This situation corresponds to the case where a person searches to find a support on a step and to the case where the prosthesis must be able to bend while opposing a sufficient resistance to compensate the weight of the person.

On the contrary, the second means 2200 permits the free flexion of the prosthesis 2 after it has attained the extension configuration, which allows the second part to become freely articulated (or with a reduced resistance) in a phase of walking during which the person who wears the prosthesis brings the prosthesis forward again to take a step.

The second means 2200 can comprise a processor functioning according to a pre-established program and permitting the processing of different operational data.

Advantageously, the prosthesis 2 for a lower limb comprises a fifth part 205 intended to ensure an ankle function.

Designated by the expression "ankle function" is at least one function of mechanical connection between second part 202 and fourth part 204 and, preferably a mechanical connection with possibility of flexion, even possibility of articulation.

The first functional means 2100 is preferably situated (but not in a limiting way) at the level of the fifth part 205 and is sensitive to mechanical stresses that this fifth part 205 receives, in such a way as to detect the bearing of the first zone 2041 of the fourth part 204 on a support 3.

The first functional means 2100 is made up, for example, of a sensor of the type called a "strain gauge", and is fixed on a structural element belonging to the fifth part 205.

One skilled in the art is able to determine, without inventive step, the type of component most suitable for achieving the function sought.

The second device 2000 further comprises a third functional means 3000 capable:

of detecting the position of the first part 201 and of the second part 202 in an angular sector of predetermined value at least contained between the first position P1 and the third position P3, of informing the second functional means 2200 of the relative position of the first part 201 and of the second part 202 in this angular sector or outside this sector.

This way, the operation of the apparatus 1 is safeguarded.

The third functional means 3000 is made up, for example, of an angle transmitter, and is situated at the level of an axis of articulation that comprises the third part 203 in view of the hinged connection of the first part 201 and of the second part 202 of the prosthesis.

One skilled in the art is able to determine, without inventive step, the type of component most suitable for achieving the function sought.

The second functional means 2200 comprises at least:

a first stop 2201 which, borne at least indirectly by the second part 202 of the prosthesis 2, adopts at least the same third position P3 as said second part 202, a second stop 2202 intended to co-operate with the first stop 2201, a first functional element 2210 to guide the second stop 2202 at least between two relative positions which are:

a fourth position P4 in which it finds itself opposed to the first stop 2201 to be able to co-operate with the latter when it presents itself in the third position P3, in such a way as to impede its movement towards the first position P1, a fifth position P5 in which it allows the movement of the first stop 2201 towards the first position P1, a second functional element 2220 to immobilize the second stop 2202 in the fourth position P4 when the first functional means 2100 does not detect the bearing of the fourth part 204 on a support 3 by said first zone 2041 of this fourth part 204.

The first stop 2201 is borne, for example, by a structural element of the prosthesis which belongs to the second part 202.

The second stop 2202 is borne, for example, indirectly by another structural element which belongs to the third part 203.

One skilled in the art is able to determine, without inventive step, the most suitable position for the first stop 2201 and the second stop 2202.

In a notable way:

the first functional element 2210, consists of a first cylinder 2211 and first piston 2212 in which the first piston 2212 bears the second stop 2202, and the first cylinder 2211 comprises a first chamber 2213, which, closed by the first piston 2212, contains a fluid 2214 under the action of the first piston 2212 and is connected to a capacitor 2215 by a transfer conduit 2216 for this fluid 2214, is made up and configured in such a way that the second stop 2202 borne by the first piston 2212 is able to be guided at least between the fourth position P4 and the fifth position P5, the second functional element 2220 is of controlled type and of type permitting the control of the passage of the fluid 2214 in the transfer conduit 2216 in such a way as to make it possible to impede the movement of the first piston 2212 or to allow this movement.

In the drawing, the fluid 2214 has been symbolized by small dots.

According to one embodiment:

the fluid 2214 is a fluid of hydraulic type, and the second functional element 2220 for control of the passage of the fluid 2214 in the transfer conduit 2216 consists of a controlled valve 2220A which, placed on the transfer conduit 2216 to be passed through by the fluid 2214, comprises an obstructor 2217 movable between a first situation S1 opposing the passage of the fluid 2214 and a second situation S2 enabling the passage of said fluid 2214.

According to another embodiment:

the fluid 2214 is a fluid of magetorheological type, and the second functional element 2220 for control of the passage of the fluid 2214 in the transfer conduit 2216 consists of a solenoid 2220B disposed locally about the conduit 2216 in such a way as to permit through a magnetic action, to coagulate the fluid 2214 locally with a view to causing the obstruction of the conduit 2216, or in the absence of magnetic action, to allow the passage of the fluid 2214 in the conduit 2216.

According to an embodiment, the first chamber 2213 accommodates a first elastic element (not represented) which exerts on the first piston 2212 an action of intensity at least sufficient to bring about, in the absence of contact between the second stop 2202 and the first stop 2201, the movement of the first piston 2212 from the fifth position P5 towards the fourth position P4.

According to another embodiment, the capacitor 2215 is of type opposing an elastic resistance to the entry of fluid 2214, and this elastic resistance is of value at least sufficient to bring about the movement of the first piston 2212 from the fifth position P5 towards the fourth position P4.

This means that the second stop 2202 borne by the first piston 2212 can advantageously follow the first stop 2201 in its displacements in order to prohibit a displacement for it only when necessary.

According to another embodiment, the capacitor 2215 is constituted by a second cylinder 2218 accommodating a second piston 2219 as well as a second elastic element 2221 which pulls the second piston 2219 in such a way that it opposes itself elastically to the entry of fluid 2214 in the capacitor 2215.

Although this is not represented, the apparatus 1 comprises an electrical energy source, such as a storage battery.

The invention claimed is:

1. An apparatus for a lower limb prosthesis, wherein the prosthesis includes a first part providing a thigh function, a second part providing a lower leg function, a third part providing a knee function, and a fourth part providing a foot function engagable with a support, the apparatus being configured for incorporation at least partially in the third part to provide a hinged connection between the first part and the second part such that the first part and the second part may have a first position in which the first part and the second part extend substantially in a prolongation one of the other and forming a first angle, and a second position in which the first part and the second part form a second predetermined angle corresponding to the maximal flexion permitted by the prosthesis, the apparatus comprising:

a first device, operatively connected between the third part and the second part, for providing a predetermined resistance at least during flexion of the prosthesis, the resistance being switched by the first device between two values which are: a predetermined maximal value selected by default, and a predetermined minimal value selected after the first part and the second part, being situated in a third position adjacent to the first position, are pulled toward the first position and are moved into this first position; and a second device including at least:

a first functional means for detecting the bearing of the fourth part on the support at least by a first zone of this fourth part which corresponds to the front of a foot, and a second functional means for:

impeding the movement of the first part and the second part toward the first position when (1) the first part and the second part are situated in a third position adjacent to the first position and the first part and the second part are pulled toward the first position, and (2) the first functional means does not detect the bearing of the fourth part on the support by the first zone, and allowing the movement of the first part and the second part toward the first position when (1) the first part and the second part are situated in a third position adjacent to the first position and the first part and the second part are pulled toward the first position, and (2) the first functional means detects the bearing of the fourth part on the support by the first zone of the fourth part.

2. An apparatus according to claim 1, wherein the prosthesis includes a fifth part providing an ankle function, wherein the first functional means is for location at the fifth part and is for sensing mechanical stresses received by the fifth part and that are indicative of the fourth part on the support to permit the detection of the bearing of the first zone of the fourth part on the support.

3. An apparatus according to claim 1, wherein the second device includes a third functional means for:

detecting whether the first part and the second part are at a relative angular position within an angular sector that extends between and includes the first and second angles, and providing an indication of the relative angular position of the first part and the second part being inside or outside of the angular sector to the second functional means.

4. An apparatus according to claim 1, wherein the second functional means includes:

a first stop borne at least indirectly by the second part of the prosthesis and movable with the second part at least to the first position and the third position, a movable second stop for co-operation with the first stop, a first functional element to guide movement of the second stop at least between two relative positions which are:

a fourth position in which the second stop is positioned to co-operate with the first stop as the first stop moves to the third position and to impede movement of the first stop as the first stop moves toward the first position, a fifth position in which the second stop allows the movement of the first stop toward the first position without impediment, a second functional element to immobilize the second stop in the fourth position when the first functional means does not detect the bearing of the first zone of the fourth part on the support.

5. An apparatus according to claim 4, wherein:

the first functional element includes a first cylinder and a movable first piston, the first cylinder provides a first chamber that is closed by the first piston, the first chamber contains a fluid, the first chamber is connected to a fluid capacitor by a transfer conduit for passage of the fluid, the second stop being located upon the first piston and the second stop is movable at least between the fourth position and the fifth position via operation of the first functional element, and the second functional element is configured and controlled to control passage of the fluid within the transfer conduit to impede or permit the movement of the first piston.

6. An apparatus according to claim 5, wherein:

the fluid is a hydraulic type fluid, and the second functional element includes a controlled valve located along the transfer conduit, the control valve includes an obstructor movable between a first situation opposing the passage of the fluid and a second situation-allowing the passage of said fluid.

7. An apparatus according to claim 5, wherein:
the fluid is a magetorheological type fluid, and
the second functional element includes a solenoid disposed locally about the conduit for:
coagulating the fluid locally with a view to causing the obstruction of the conduit via a magnetic action, and
allowing the passage of the fluid in the conduit in the absence of magnetic action.

8. An apparatus according to one of claims 5 to 7, wherein the first functional element is configured to provide for movement of the first piston from the fifth position toward the fourth position in the absence of contact between the second stop and the first stop.

9. An apparatus according to one of claims 5 to 7, wherein the capacitor provides an elastic resistance to the entry of fluid into the capacitor and this elastic resistance is of value at least sufficient to bring about the movement of the first piston from the fifth position toward the fourth position.

10. An apparatus according to claim 9, wherein the capacitor includes a second chamber, a second piston and an elastic element, the elastic element presses on the second piston with an intensity at least sufficient to bring about, in the absence of contact between the second stop and the first stop, movement of the first piston from the fifth position toward the fourth position.

11. A prosthesis for a lower limb, wherein the prosthesis includes an apparatus as set forth in one of claims 1 to 4.

* * * * *